United States Patent [19]

Baile et al.

[11] Patent Number: 4,898,961
[45] Date of Patent: Feb. 6, 1990

[54] METHOD FOR PREPARING ALKENYLSILANES

[75] Inventors: Gnaneshwar R. Baile, Midland; Donald E. McVannel, Hemlock, both of Mich.; Kirsten L. Reading, North Royalton, Ohio; Ginger L. Hall, Barry, Wales

[73] Assignee: Dow Corning Corporation, Midland, Mich.

[21] Appl. No.: 380,929

[22] Filed: Jul. 17, 1989

[51] Int. Cl.$^4$ ................................................ C07F 7/08
[52] U.S. Cl. ...................................................... 556/479
[58] Field of Search ........................................ 556/479

[56] References Cited

U.S. PATENT DOCUMENTS

| | | | |
|---|---|---|---|
| 2,632,013 | 3/1953 | Wagner et al. | 556/479 |
| 2,721,873 | 10/1955 | MacKenzie et al. | 556/479 |
| 3,404,169 | 5/1969 | Gaignon et al. | 556/479 |
| 3,410,886 | 11/1968 | Joy | 556/479 |
| 3,567,755 | 3/1971 | Seyfried et al. | 556/479 X |
| 3,793,358 | 2/1974 | Bauer et al. | 556/479 |
| 4,276,426 | 8/1981 | Lindner et al. | 556/479 |
| 4,422,899 | 1/1983 | Juhola et al. | 556/479 |
| 4,579,965 | 9/1986 | Kanner et al. | 556/479 |

FOREIGN PATENT DOCUMENTS

| | | | |
|---|---|---|---|
| 93718 | 4/1977 | Japan | 556/479 |
| 133296 | 7/1981 | Japan | 556/479 |
| 46888 | 12/1981 | Japan | 556/479 |
| 4995 | 3/1982 | Japan | 556/479 |

Primary Examiner—Paul F. Shaver
Attorney, Agent, or Firm—Robert Spector

[57] ABSTRACT

The present invention provides a method for preparing alkenylsilanes whereby a gaseous mixture consisting essentially of an acetylenic hydrocarbon and a silane containing a silicon-bonded hydrogen atom is directed into contact with a reaction medium in the form of a relatively thin moving liquid layer or film. The reaction medium comprises a solubilized hydrosilylation catalyst and the alkenylsilane produced as a product of the reaction. The reaction medium can optionally include an organic liquid that is a solvent for the catalyst, alkenylsilane and acetylenic hydrocarbon reactant.

6 Claims, No Drawings

METHOD FOR PREPARING ALKENYLSILANES

BACKGROUND OF THE INVENTION

1. Field of the Invention

This invention relates to a method for preparing alkenylsilanes. More particularly, this invention relates to the preparation of alkenylsilanes by the reaction of a gaseous acetylenic hydrocarbon with a gaseous silane containing a silicon-bonded hydrogen atom in the presence of a hydrosilylation catalyst under conditions that maximize the yield of the desired alkenylsilane and minimize both undesirable by-products and the hazards associated with processing gaseous acetylenic hydrocarbons.

2. Description of the Prior Art

It is known to prepare alkenylsilanes in general and vinyl silanes in particular by the reaction of an acetylenic hydrocarbon with a silane containing a silicon-bonded hydrogen atom, referred to hereinafter as an SiH-containing silane. This reaction can also produce appreciable amounts of the corresponding disilyalkane from the further reaction of the alkenylsilane with additional SiH-containing silane. U.S. Pat. No. 3,793,358, which issued to Bauer et al. on Feb. 19, 1974 discloses that formation of the disilylalkane can be avoided by conducting the reaction of an acetylenically unsaturated hydrocarbon and a silane containing one or two silicon-bonded hydrogen atoms in the presence of a platinum-containing hydrosilylation catalyst and a diluent consisting essentially of the disilylalkane that would be produced as a by-product of the reaction. The reaction is conducted at a temperature of from 120° to 220° C. and under a pressure of from 0.1 to 5 atmospheres gauge, equivalent to an actual pressure of from 1.1 to 6 atmospheres, and the alkenylsilane produced as a product is continuously removed from the reactor as a gas. In all of the examples a gaseous mixture of the acetylene and the silane is bubbled into the lower end of a tower that is partially filled with the disilylalkane and the catalyst.

U.S. Pat. No. 3,404,169, which issued to Gaignon et al. on Oct. 1, 1969 teaches preparing vinylsilanes by the reaction of acetylene with a halosilane containing a silicon-bonded hydrogen atom in the presence of a platinum catalyst and an inert liquid diluent such as an aromatic hydrocarbon under atmospheric pressure and reaction temperatures of from 80° to about 120° C. The examples of this application describe adding a mixture of gaseous acetylene and the silane reactant in liquid form through a tube that extends below the surface of a stirred mixture formed by blending chlorobenzene with finely divided platinum as the hydrosilylation catalyst. The present inventors discovered that the yield of the desired alkenylsilane produced under the conditions described in this patent is relatively low, and the reaction produces relatively large amounts of the aforementioned disilylalkane by-product.

U.S. Pat. No. 4,276,426 teaches a continuous process for hydrosilylation reactions catalyzed by chloroplatinic acid. In accordance with this process the reactants are continuously introduced into a tube type reactor wherein the contents are maintained at temperatures of from 120° to 170° C. The reactants are maintained in the liquid phase using superatmospheric pressure as required and are circulated at speeds of at least 1000 cm/minute. The exemplified ractants are esters of ethylenically unsaturated carboxylic acids and SiH-containing silanes. The conditions specified in this patent would not be suitable for acetylenic hydrocarbons, which would tend to decompose and/or react with explosive violence under these conditions.

U.S. Pat. No. 4,579,965, which issued to Kanner et al. on Apr. 1, 1986 teaches preparing vinyltri(t-alkoxy)silanes accompanied by only minor amounts of the corresponding bis(tri-t-alkoxysilyl)ethane by reacting acetylene with the corresponding organohydrogensilane in the presence of a platinum compound as the hydrosilylation catalyst at temperatures above 150° C. A major disadvantage of this process is the chemical instability of the hydrosilylation catalyst at the reaction temperature. The catalyst is reduced to metallic platinum.

Japanese Unexamined Patent Publication No. 46,888/81, which issued on Apr. 28, 1981 discloses reacting a hydrogenhalosilane with from 8 to 20 moles of acetylene for each mole of the silane. This process requires recovery and recirculation of the large amount of unreacted gaseous acetylene to make the process economically practical and/or comply with environmental regulations governing discharge of hazardous acetylene into the atmosphere.

Japanese Patent Publication No. 133,296/81, which issued on Oct. 19, 1981 teaches using triphenylphosphine complexes of platinum, palladium or ruthenium as hydrosilylation catalysts for the reaction of acetylene with a monohydrocarbyldichlorosilane. Using triphenylphosphine complexes of specified group of platinum compounds is taught in Japanese Patent Publication No. 4,995/82, which issued on Jan. 11, 1982.

An objective of the present invention is to provide a method for the preparation of alkenylsilanes, particularly vinylhalosilanes or vinylalkoxysilanes that optionally contain 1 or 2 silicon-bonded hydrocarbon radicals. The process involves the reaction of an acetylenic hydrocarbon with an SiH-containing silane under conditions that yield only minor amounts of undesired by-products, particularly disilylalkanes, yet are not conducive to the explosive decomposition of the acetylenic hydrocarbon reactant.

SUMMARY OF THE INVENTION

The present method is characterized by a reaction medium in the form of a relatively thin moving liquid layer that is contacted by a gaseous blend of the acetylenic hydrocarbon and SiH-containing silane. The reaction medium comprises a solubilized hydrosilylation catalyst and the alkenylsilane produced as a product of the reaction. The reaction medium can optionally include an organic liquid that is a solvent for the catalyst, alkenylsilane and acetylenic hydrocarbon reactant.

DETAILED DESCRIPTION OF THE INVENTION

This invention provides an improved method for preparing an alkenylsilane by the reaction of a acetylenic hydrocarbon with a silane containing a silicon-bonded hydrogen atom, where the reaction is conducted in the presence of a liquid medium comprising said alkenylsilane and a solubilized hydrosilylation catalyst. The improvement comprises a. conducting said reaction under a pressure below the critical explosive decomposition pressure of said acetylenic hydrocarbon by introducing a homogeneous gaseous mixture consisting essentially of said acetylenic hydrocarbon and said silane into a reactor wherein said mixture is directed into contact with the surface of at least one moving layer of a liquid reaction medium comprising said alkenylsilane and said catalyst, where said reaction medium is an effective solvent for said acetylenic hydrocarbon, b. maintaining the relative concentrations of acetylenic hydrocarbon and gaseous silane in said mixture equivalent to a molar ratio of hydrocarbon to silane of greater than 1, and c. adjusting the flow rates of said homogeneous mixture and said liquid layer to maintain the temperature within said reactor at a level favoring formation of said alkenylsilane and which is not conducive to further reaction of said alkenylsilane and decomposition of said acetylenic hydrocarbon.

Characterizing Features of the Present Method

The reaction conditions that characterize the present method are the form of the liquid reaction medium and the manner in which the mixture of acetylenically unsaturated hydrocarbon and SiH-containing silane comes into contact with this reaction medium.

The reaction medium comprises the hydrosilylation catalyst and the alkenylsilane produced as the principal product of the present method. As discussed hereinafter the reaction medium optionally contains an organic liquid that is a solvent for the alkenylsilane, the hydrosilylation catalyst and the acetylenic hydrocarbon reactant.

The improvement in product yield and reduction in the amount of undesirable by-products, particularly disilylalkane, is due to the presence of a relatively thin moving liquid layer or film as the reaction medium. This form of reaction medium greatly increases the rate at which the heat generated by the exothermic reaction of the acetylenic hydrocarbon with the SiH-containing silane is transferred away from the reaction site. If not removed this heat can cause decomposition of the acetylenic hydrocarbon and/or an increase in the rate of reaction of the alkenylsilane produced as a product of the present method with the SiH-containing silane to form a disilylalkane.

In a preferred embodiment of a reactor for carrying out the present method, a mixture of the two gaseous reactants is directed into contact with at least one thin layer of reaction medium as the layer is flowing down a surface within the reactor. Preferably the surface is oriented in a vertical direction. The thickness of the moving layer is generally less than 2 mm. The reactor medium should be uniformly distributed throughout the layer to ensure uniform generation and transfer of heat. It should be understood that the optimum ranges for thickness of the moving layer of reaction medium and the speed at which this layer is moving may vary somewhat from these typical ranges depending upon the size of the reactor and the flow rate of the gaseous reactants. While the relative directions of the gaseous reactants and reaction medium are not critical with respect to the operability of the present method, most preferably the liquid layer and the gaseous reactant mixture are moving in opposing directions. The angle of contact between the moving liquid layer and the stream of gaseous reactants is generally from 90° to 180° C. The flow rate of the liquid layer in a laboratory scale reactor is generally within the range of from about 4 to about 24 cc per minute per square centimeter of reactor surface area.

The rate at which the mixture of gaseous reactants is introduced into the reactor and into contact with the moving layer of reaction medium will influence the amount of heat generated by the reaction of the acetylenic hydrocarbon and the SiH-containing silane. The rate of gaseous reactant flow in a laboratory scale reactor is generally from about 400 to about 1000 cc/minute, measured under conditions of standard temperature and pressure (25° C. and 1 atmosphere). The optimum flow rate for the gaseous reactants is determined at least in part by the capacity of the reactor.

The surface along which the liquid reaction medium is flowing can be the inner or outer surface of one or more tubes located within the reactor or the outer shell of the reactor itself.

Because the reaction between the gaseous acetylenic hydrocarbon is exothermic, it should be apparent that the total surface area of the liquid layer and the rate at which the gaseous reactants are absorbed into the liquid layer are the two most important factors determining the temperature of the moving liquid layer. In accordance with the present method this temperature is generally from about 30° to about 120° C. Using acetylene as the acetylenic hydrocarbon this temperature range is preferably from 50° to about 80° C. Operating outside of this temperature range increases the yield of the undesired disilylalkane.

It is generally preferred to heat the liquid reaction mixture to within the desired temperature range for the reaction prior to introduction of the gaseous reactant mixture. Once the reaction has initiated, cooling of the liquid reaction mixture may be required to maintain the temperature within the desired range.

The Acetylenic Hydrocarbon

Any terminally unsaturated acetylenic hydrocarbon that exists as a gas under the reaction conditions of the present method (a pressure of less than two atmospheres and temperatures of from 30 to about 120 degrees C.) can be reacted with an SiH-containing silane in accordance with the present method. These acetylenic hydrocarbons can be represented by the formula $R^1CH{\equiv}CH$, where $R^1$ represents a hydrogen atom or an alkyl radical containing from 1 to 4 carbon atoms. Acetylene is generally the preferred hydrocarbon, based on its cost, availability, high reactivity and the commercial utility of vinylsilanes produced using this reactant.

The SiH-Containing Silane Reactant

Any silane containing a silicon-bonded hydrogen atom and existing as a gas under the conditions of the present method can be used as the silane reactant. These silanes can be represented by the general formula $HSiR^2{}_nX_{3-n}$, where $R^2$ represents a monovalent hydrocarbon radical or a monovalent halogenated hydrocarbon radical, X represents a halogen atom or an alkoxy group containing from 1 to 4 carbon atoms and n is 0, 1 or 2. In preferred silanes $R^1$ when present represents methyl and X represents chlorine or methoxy. If the particular silane selected does not boil below about 120 degrees C under ambient pressure, the temperature at which the silane will boil can be reduced by reducing the pressure within the reactor to below atmospheric pressure.

Preferred silanes include but are not limited to trichlorosilane, trimethoxysilane, methyldichlorosilane, dimethylchlorosilane and methyldimethoxysilane, this preference being based on the cost and availability of the intermediates required to prepare the silanes and the utility of the final alkenylsilanes.

The Relative Concentrations of Acetylenic Hydrocarbon and SiH-Containing Silane

The present inventors discovered that the yield of the desired alkenylsilane can be maximized with only minor amounts of disilylalkane by-product being formed when the molar ratio of acetylenic hydrocarbon to SiH-containing silane is at least 1:1. When the reaction is between acetylene and either methyldichlorosilane or dimethylchlorosilane this ratio is preferably between 1.1:1 and 1.3:1. Irrespective of the reactants, relative concentrations of acetylenic hydrocarbon greater than about 3 moles of the hydrocarbon per mole of SiH-containing silane offer no substantial improvement in yield or purity of the desired alkenylsilane to compensate for the presence of unreacted acetylenic hydrocarbon following completion of the reaction.

The excess hydrocarbon reactant must either be recovered and recycled or disposed of by chemical reaction or venting. The toxicity and explosive nature of acetylenic hydrocarbons can unduly complicate disposal of these materials and add is significantly to the cost of producing the alkenylsilane. One method for reducing the amount of unreacted acetylenic hydrocarbon involves using two reactors connected in series whereby the unreacted acetylenic hydrocarbon emerging from the first reactor is blended with additional silane containing silicon-bonded hydrogen, passed into the second reactor and processed in accordance with the present method.

The Hydrosilylation Catalyst

Any of the known hydrosilylation catalysts that are soluble in the liquid reaction medium can be used to promote the reaction between the acetylenic hydrocarbon and the SiH-containing silane. One of the most commonly used classes of hydrosilylation catalyst are metals from the platinum group of the periodic table and compounds of these metals.

Platinum halides such as chloroplatinic acid are a preferred group of catalysts for the present method based on the catalytic activity of these compounds and their solubility in the reaction medium formed by the alkenylsilane and one or more of the optional organic liquids discussed in a subsequent portion of this specification.

The optimum concentration of hydrosilylation catalyst is at least partially dependent on the composition of the two reactants and any organic liquids present in the liquid reaction medium, and on the reaction conditions. Typically the amount of catalyst required to promote the reaction between an acetylenic hyrocarbon and an SiH-containing silane is equivalent to from about 1 to about 100 gram atoms of platinum per one million moles of silicon-bonded hydrogen present in the reactor. It will be understood that additional catalyst will have to be added during a continuous process to replace the amount lost as the reaction medium is withdrawn from the reactor.

Optional Solvents for the Reaction Medium

In addition to a solubilized hydrosilylation catalyst and the alkenylsilane produced as the desired product of the present method, the liquid reaction medium can include at least one organic liquid that is a solvent for the catalyst and the alkenylsilane. To reduce the yield of by-products, particularly the corresponding disilylalkane, the organic liquid should also be an effective solvent for the acetylenic hydrocarbon. One additional requirement for the organic liquid is it not boil or evaporate rapidly at the temperature generated in the reaction zone.

Preferred organic liquids include but are not limited to liquid aliphatic and aromatic hydrocarbons, alkyl ethers of alkylene glycols, ethers and ketones. Preferred organic liquids include but are not limited to the toluene, xylene, the dimethyl ether of ethylene glycol, tetrahydrofuran, methyl ethyl ketone and methyl iso-butyl ketone. These organic liquids can be used individually or as mixtures so long as the individual liquids are compatible with one another.

When one or more organic liquids are present in the liquid reaction medium of this invention they typically constitute from 10 to about 80 weight percent of the liquid reaction medium, preferably from 10 to 40 weight percent.

Reactor Requirements

As disclosed in a preceding section of this specification the reaction between the acetylenic hydrocarbon and SiH-containing silane occurs in a liquid reaction medium that is in the form of a moving layer or film. In accordance with one embodiment of the present method the layer or film is formed by directing a stream of the liquid reaction medium along the interior wall of at least one vertically oriented tube located within a reactor. The reactor contains at least one of these tubes that is supported by impervious plates located at the upper and lower ends of the tubes. The plates contact the exterior walls of the tubes around their entire circumference and extend to the shell of the reactor. The configuration of the plates divides the reactor into an upper, middle and a lower chamber.

The upper reactor chamber is equipped with a port through which the liquid reaction medium enters the reactor, flows over the upper surface of the upper plate and enters the tubes. The upper chamber of the reactor also contains a port through which unreacted gaseous materials can be vented from the reactor.

The end of the tube through which the liquid reaction medium enters is preferably equipped with at least one weir to direct the flow of the reaction medium along the wall of the tube. The outer wall of the tube is in contact with a circulating liquid coolant, preferably water, to remove the heat generated by the exothermic reaction occurring within the tube and transferred through the tube wall. The coolant is circulated through the middle chamber of the reactor. This configuration is sometimes referred to as a "tube side reactor". An examples of this type of reactor is the vertical tube type of heat exchanger described in U.S. Pat. No. 4,422,899, the disclosure of which is hereby incorporated by reference. Reactors suitable for use in connection with the present process contain non-perforated continuous pipes rather than the nozzles and overflow pipes that characterize the heat exchanger of the referenced patent. The lower chamber of the reactor is equipped with a port through which the reaction medium can be withdrawn from the reactor and recycled. The mixture of gaseous reactants is introduced into the lower chamber of the reactor and directed upwards through each of the tubes. Preferably the reactants are introduced through vertically oriented nozzles that are positioned directly below the lower end of each tube carrying the liquid reaction mixture.

The pressure within the reactor is below the pressure at which the acetylenic hydrocarbon is likely to undergo explosive decomposition at the temperature of the reaction. Using acetylene as the acetylenic hydrocarbon, this pressure is typically from atmospheric to about 2 atmospheres absolute pressure. Atmospheric pressure is preferred based on safety considerations and the absence of the additional equipment required to react gaseous materials under pressure, thereby simplifying reactor design.

In accordance with an alternative type of reactor operation, the mixture of gaseous reactants is introduced into the aforementioned middle chamber defined by the outer walls of the tubes and inner surface of the reactor shell. In accordance with a preferred embodiment, a stream of gaseous reactants is directed against each layer or film of liquid reaction medium. The liquid reaction medium enters at the top of this chamber and is directed in a downward flow along outer walls of the tubes and optionally along the inner shell wall, and a stream of gaseous reactants is directed against each layer or film of liquid reaction medium. This alternative configuration is sometimes referred to as a "shell side reactor". The advantage of this type of configuration include more efficient mass transfer and more control of the mixing of the gaseous and liquid phases. In this embodiment the cooling medium flows through the tubes.

In a shell side reactor configuraton the directions of the gaseous reactant stream and the liquid reaction medium can define an angle of between 90 and 180 degrees. In a preferred reaction of this type the exterior of the tubes is equipped with baffles to maintain the reaction medium in contact with the surface of the tubes as the reaction medium is being contacted with the gaseous reactants.

EXAMPLES

The following example is intended to describe one embodiment of the present invention and should not be interpreted as limiting the scope of the invention as defined in the accompanying claims. Unless otherwise specified all parts and percentages specified in the example are by weight.

The reaction between acetylene and methyldichlorosilane was conducted using laboratory scale vertical tube reactor containing three tubes, 20 cm. in length that were completely surrounded by an outer shell. The tubes were supported at their upper and lower ends by horizontally oriented, impermeable plates measuring 10 cm. in diameter that completely surrounded the tubes and contacted the outer shell of the reactor along its entire perimeter, thereby dividing the reactor into the upper, middle and lower chambers. The upper and lower ends of the tubes projected for a distance of about 5 mm. from the respective plates and the lower end of the tubes terminated at a distance of 10 cm. from the bottom of the reactor. The lower chamber of the reactor was equipped with a gas conduit equipped with 3 nozzles that directed individual streams of the acetylene/methyldichlorosilane mixture into the open end of each of the three tubes in the reactor. The nozzles were located 1 cm. below the lower end of the tubes. The lower section of the reactor also contained an outlet port through which the liquid reaction medium was withdrawn and recycled by means of a pump to an inlet port located in the upper chamber of the reactor.

In addition to the inlet port the upper chamber was equipped with an outlet port through whih unreacted gaseous materials could be vented.

The middle chamber of the reactor was equipped with inlet and outlet ports through which water was circulated to contact the outer surfaces of the tubes during operation of the reactor.

The liquid reaction medium that entered through the inlet port in the upper chamber of the reactor entered the upper end of the tubes by flowing over weirs that directed the stream of liquid along the inner walls of the tubes.

During operation of the reactor the three streams of acetylene and methyldichlorosilane entering the lower chamber of the reactor through the gas feed nozzles were directed upward through the tubes containing the descending streams of reaction medium.

The initial reaction medium was prepared by blending of the amounts of methylvinyldichlorosilane and solvent listed in Table 1. 100 parts of this mixture and 0.05 part of catalyst solution. The solvent was xylene (1), methylethyl ketone (2) or the dimethyl ether of ethylene glycol (3). The catalyst solution was an isopropanolic chloroplatinic acid solution containing 0.1 mmol of platinum per millilliter of solution.

The process was begun by pumping the reaction medium through the reactor at a rate of two liters per minute. The water flowing through the middle chamber of the reactor was thermostatically maintained at a temperature of 67° C. The temperature of the liquid reservoir in the lower chamber of the reactor was monitored by means of a thermocouple that controlled the temperature of the circulating water. When the temperature of the reaction medium reached 67° C. the flow of gaseous acetylene/silane mixture was begun. The molar ratio of acetylene to silane was 1.3:1, respectively and the mixture of gaseous reactants was introduced at a rate of 680 cc. per minute. The volume of reaction medium was maintained at the initial level by allowing the excess to drain through the overflow port in the wall of the reactor. This material was collected and distilled at the end of the 8-hour reaction period to recover the methylvinyldichlorosilane formed as the major product of the reaction.

The weight ratio of methylvinyldichlorosilane (A) to 1,2-bis(methyldichlorosilyl)ethane (B), the latter being a by-product of the reaction, were determined using gas-liquid chromatography and are recorded in Table 1.

TABLE 1

| Solvent Type | Solvent/Vinylsilane[a] (%) | Vinylsilane/Disilylethane (weight ratio) |
|---|---|---|
| 1 | 20/80 | 16/1 |
| 1 | 50/50 | 27/1 |
| 2 | 10/90 | 20/1 |
| 3 | 10/90 | 23/1 | a - Composition of initial reaction medium
1 - Xylene
2 - methylethyl ketone
3 - dimethyl ether of ethylene glycol The data in Table 1 demonstrate that the yield of vinylsilane relative to the disilylethane by-product can be increased by using a solvent that is a more effective solvent for acetylene. The dimethyl ether of ethylene glycol is a more effective solvent for acetylene than methylethyl ketone, which in turn is a more effective solvent than xylene.

That which is claimed is:

1. In a method for preparing an alkenylsilane by the reaction of an acetylenic hydrocarbon with a silane containing a silicon-bonded hydrogen atom, where the reaction is conducted in the presence of a liquid medium comprising said alkenylsilane and a solubilized hydrosilylation catalyst, the improvement comprising a. a conducting said reaction under a pressure below the critical decomposition temperature of said acetylenic hydrocarbon by introducing a homogeneous gaseous mixture consisting essentially of said acetylenic hydrocarbon and said silane into a reactor wherein said mixture is directed into contact with the surface of at least one moving layer of a liquid medium comprising said alkenylsilane and said catalyst, where said medium is an effective solvent for said acetylenic hydrocarbon, b. maintaining the relative concentrations of acetylenic hydrocarbon and gaseous silane in said mixture equivalent to a molar ratio of hydrocarbon to silane of greater than 1, and c. adjusting the flow rates of said homogeneous mixture and said liquid medium to maintain the temperature within said reactor at a level favoring formation of said alkenysilane and which is not conducive to further reaction of said alkenylsilane and decomposition of said acetylenic hydrocarbon.

2. A method according to claim 1 where the acetylenic hydrocarbon is represented by the formula $R^1CH\equiv CH$, and said gaseous silane is represented by the formula $HSiR^2{}_nX_{3-n}$, where $R^1$ represents hydrogen or an alkyl radical containing from 1 to 4 carbon atoms, $R^2$ represents a monovalent hydrocarbon radical or a monovalent halogenated hydrocarbon radical, X represents a halogen atom or an alkoxy group containing from 1 to 4 carbon atoms and n is 0, 1 or 2, said liquid medium contains an organic liquid that is an effective solvent for said acetylenic hydrocarbon, said catalyst and said alkenylsilane, the thickness of said moving layer is less than 2 mm. and the rate of flow of said layer is from 4 to 24 cc. per minute per square centimeter of reactor surface area.

3. A method according to claim 2 wherein the molar ratio of acetylenic hydrocarbon and gaseous silane is from 1.1:1 to 1.3:1, $R^1$ is hydrogen, $R^2$ is alkyl, phenyl or 3,3,3-trifluoropropyl, n is 1 or 2, said organic liquid is a liquid hydrocarbon, an etherified glycol or a ketone wherein the hydrocarbon groups of said glycol and ketone are alkyl containing from 1 to 4 carbon atoms, and said hydrosilylation catalyst is a compound of platinum or rhodium.

4. A method according to claim 3 where $R^2$ is methyl, the temperature of said liquid medium is from 30° to about 120° C., a portion of the liquid medium is removed periodically or continuously to recover said alkenylsilane and is replaced by substantially equal volume of a solution comprising said catalyst and said organic liquid, and said hydrosilylation catalyst is chloroplatinic acid.

5. A method according to claim 4 where the said organic liquid constitutes from 10 to 40 weight percent of said liquid medium and the temperature of the liquid medium is from 60° to 80° C., the reaction of said mixture is conducted under atmospheric pressure, the temperature of said liquid medium is controlled by heating or cooling the surfaces contacted by said medium, and any unreacted acetylenic hydrocarbon is passed from said reactor into a second reactor where it is blended with additional gaseous silane and reacted in accordance with said method.

6. A method according to claim 5 where said method is carried out in a vertical tube type reactor wherein said liquid medium flows within the tubes and the exterior of the tubes is in contact with water at a temperature required to maintain the temperature of the liquid medium at from 50° to 80° C.

* * * * *